(12) United States Patent
Ishii et al.

(10) Patent No.: US 8,137,701 B2
(45) Date of Patent: Mar. 20, 2012

(54) METHOD OF PRODUCING A DRY EARTHWORM POWDER

(75) Inventors: Yoichi Ishii, Miyazaki (JP); Hiroyuki Sumi, Kurashiki (JP); Etsuo Yoshida, Miyazaki (JP)

(73) Assignee: Well Stone Co., Miyazaki (JP)

( * ) Notice: Subject to any disclaimer, the term of this patent is extended or adjusted under 35 U.S.C. 154(b) by 977 days.

(21) Appl. No.: 12/076,738

(22) Filed: Mar. 21, 2008

(65) Prior Publication Data

US 2009/0238891 A1 Sep. 24, 2009

(51) Int. Cl.
*A61K 35/56* (2006.01)

(52) U.S. Cl. ............ 424/520; 424/94.64; 514/2; 514/12

(58) Field of Classification Search .................... None
See application file for complete search history.

(56) References Cited

U.S. PATENT DOCUMENTS

| | | |
|---|---|---|
| 5,024,844 A | 6/1991 | Ishii et al. |
| 5,128,148 A | 7/1992 | Ishii et al. |
| 5,186,944 A | 2/1993 | Ishii et al. |
| 5,576,026 A | 11/1996 | Charter et al. |

FOREIGN PATENT DOCUMENTS

| | | |
|---|---|---|
| EP | 0 383 533 | 8/1990 |
| JP | 64-47718 | 2/1989 |
| JP | 64-47719 | 2/1989 |
| JP | 64-47720 | 2/1989 |
| JP | 1-268639 | 10/1989 |
| JP | 3-72427 | 3/1991 |

*Primary Examiner* — Hope Robinson
(74) *Attorney, Agent, or Firm* — Wenderoth, Lind & Ponack, L.L.P.

(57) ABSTRACT

Provided is a method of producing a dry earthworm powder without deterioration in useful pharmacological action, by removing dirt on the skin of earthworms while allowing the earthworms to excrete the digest remaining in the digestive tracts efficiently without weakening the earthworms, which comprises the steps of: standing living earthworms under light for 10 to 50 hours, removing the dirt formed on the skin thereof, adding an organic acid to the living earthworms, diluting the acid rapidly with addition of water, adjusting the pH of the aqueous acidic solution to 2 to 5, standing the earthworm mixture for 3 to 180 minutes under the pH condition, washing the earthworms with water, grinding the earthworms into a homogenate, freezing the homogenate at −18° C. to −35° C., keeping the frozen homogenate for 20 to 240 hours, and freeze-drying and degassing the frozen homogenate under vacuum simultaneously.

2 Claims, No Drawings

METHOD OF PRODUCING A DRY EARTHWORM POWDER

BACKGROUND OF THE INVENTION

The present invention relates to a method of producing a dry earthworm powder effective in treatment of various diseases, by removing the dirt in digestive tracts and on the skin of the earthworms without deterioration in the pharmacological action inherent to the earthworms.

Earthworms have been used from ancient times in oriental countries as drugs for prevention and treatment of various diseases, and have found applications such as intracystic calculus-contraction and releasing-stimulating agent, anti-choloplania agent, parturifacient, tonic, hair growth tonic, pickup, antifebrile, spasm-treating agent, blood flow accelerator, hemiplegia-treating agent, indirect analgesic, urination improving agent, anti-bronchial asthma agent, anti-hypertension agent and others.

It is necessary to remove the digest of an earthworm remaining in the digestive tracts, the dirt on the skin, and others for production of a medicine for oral administration by using the living body of the earthworm as the raw material, and various methods for that purpose have been proposed.

Examples thereof so far proposed include methods of producing a dry earthworm powder useful as an anti-diabetes agent, anti-hyperlipidemia agent, or blood pressure-adjusting agent, by immersing living bodies of earthworms in an aqueous solution of an alkali salt such as sodium salt or potassium salt, allowing them to excrete the cast in the digestive tracts, wet-grinding the earthworms, and freeze-drying the suspension thus obtained under vacuum (JP1-47718A, JP1-47719A, JP1-47720A and JP1-268639A), and a method of producing a medicine for patients with thrombosis, by immersing living bodies of earthworms in an aqueous acid solution kept at 6 to 26° C. for 0.1 to 5 hours, allowing them to excrete the cast in the digestive tracts, grinding the earthworms, degassing the homogenate, and vacuum-drying the homogenate, while the temperature is raised stepwise (JP3-72427A).

However, immersion of living bodies of earthworms in an aqueous alkali salt or acid solution for an extended period of time leads to weakening of the earthworms, consequently to denaturation of the proteins contained in the body, deterioration in enzyme activities and also in the pharmacological action of the earthworm powder obtained.

SUMMARY OF THE INVENTION

An object of the present invention is to provide a method of producing a dry earthworm powder in the state having a favorably pharmacological action, by allowing living bodies of earthworms to excrete the digest remaining in the digestive tracts and the dirt on the skin efficiently without weakening the earthworms.

After intensive studies to make living bodies of earthworms excrete the digest remaining in the digestive tracts effectively without weakening the earthworms, the inventors have found that, if living earthworms are placed under light, then brought into contact with an organic acid, an environment unfavorable for the earthworms, before processing, and grown under the condition for a particular time, the earthworms excrete the digest in the digestive tracts and cover themselves with the excretion to cope with the environment, and thus, that it was possible to obtain purified living bodies of the earthworms by removing the dirt or the excretion on the skin, and made the present invention, based on the finding.

Thus, the present invention provides a method of producing a dry earthworm powder which comprises the steps of: standing living earthworms under light for 10 to 50 hours, removing the dirt formed on the skin thereof, adding an organic acid to the living earthworms, diluting the acid rapidly with addition of water, adjusting the pH of the aqueous acidic solution to 2 to 5, standing the earthworm mixture for 3 to 180 minutes under the pH condition, washing the earthworms with water, grinding the earthworms into a homogenate, freezing the homogenate at −18° C. to −35° C., keeping the frozen homogenate for 20 to 240 hours, and freeze-drying and degassing the frozen homogenate under vacuum simultaneously.

DETAILED DESCRIPTION OF THE PREFERRED EMBODIMENTS

Hereinafter, the method according to the present invention will be described in detail.

In the method according to the present invention, a living earthworm is used as the raw material, and the living earthworm used is arbitrarily selected from organisms belonging to Annelida Oligochaeta, generally called earthworms, such as *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima sieboldi* Horst, *Pheretima hilgendofi, Pontodrilus matsushimensis* Iizuka, *Tubifex hattai* Nomura, *Limnodrilus gotoi* Hatai or *L. Socialis* Stephenson and so on.

In the method according to the present invention, first, living earthworms are placed under light for a particular period. Specifically, living earthworms withdrawn from a worm bed are placed in a tray-shaped flat box and kept there for 10 to 50 hours under sunlight or under illumination at night. The internal capacity of the flat box then is an amount corresponding to a thickness of about 30 to 60 mm, preferably 40 to 50 mm. When placed under light, the earthworms, which are nocturnal, try to protect themselves by covering the skin with dirt for blockage of light or prevention from water vaporization, and repeated removal of the dirt by a suitable means several times finally prompts the earthworms to release solid matter and body fluid out of the enteric tracts and cover the skin therewith. Then in the flat box, the multiple living earthworms stacked on each other try to crawl deeper below other earthworms, looking for a darker place while in contact with each other, which in turn leads to separation of the dirt and the excretion on the skin by friction. If the living earthworms are enclosed for example with a nonwoven fabric, the dirt and the excretion separated by friction can be adsorbed and removed easily.

In the method according to the present invention, the living earthworms, from which the dirt and the excretion are removed, are then washed with water, and brought into an living environment unpleasant to the living earthworms by the addition of an organic acid. The addition of the organic acid may be carried out by scattering an organic acid powder as it is or a concentrated aqueous organic acid solution on the living earthworms.

Examples of the organic acid used then include acetic acid, malic acid, citric acid, lactic acid, malonic acid, succinic acid, and the like. These acids may be used alone or as a mixture of two or more acids. The particularly favorable organic acid is citric acid.

In such a case, prolonged contact between the living earthworms and an organic acid powder or a conc. aqueous organic acid solution leads to death or weakening of the earthworms and thus to no excretion of the digest in the digestive tracts, and therefore, the living earthworms are preferably washed with water as soon as possible after contact with the organic acid, normally within 30 seconds or less, preferably 20 seconds or less, until the pH of the earthworms becomes in the range of 2 to 5. The dilution with water should be carried out promptly. Sufficient care should be given to the fact that the delay may lead to death of the earthworms.

Thus in the method according to the present invention, it is possible to ensure sterilization action by once sterilizing living earthworms by using the sterilization action of an organic acid and then sterilizing them further by freeze drying under vacuum.

In the method according to the present invention, because the earthworms are placed under light, i.e. a living environment unfavorable for activity of the nocturnal living earthworm, and additionally brought into an living environment extremely unpleasant to the living earthworms, the living earthworms release solid and liquid matters of the dirt and the excretion for protection of themselves and for improvement of the living environment to purify themselves automatically.

Use of an organic acid, which has a sterilizing action, in the method according to the present invention leads to excretion of the digests remaining in the digestive organs as described above and sterilization of the unwanted bacteria that are not removed simply by water washing.

Presence of water is indispensable for the self-protecting function, but about 65% of the living earthworm structure is water, and thus, there is some periodical allowance for the self-protecting function. However, because death of the living earthworms is undesirable, care should be given to the control of the period during which the living earthworms are placed under an unpleasant living environment. The period may vary according to the condition used, but normally in the range of 3 to 180 minutes.

As described above, when living earthworms are brought into an unpleasant living environment by the addition of an organic acid, the digest remaining in the digestive tracts, ammonia, a cause for foul odor, and arsenic-containing body fluid that is toxic to the body are excreted, and most of ammonia is removed by the acid.

Conventionally, cleaned living earthworms were pulverized and frozen as they were, leaving ammonia unremoved, and the ammonia was removed in the following freeze drying step under vacuum, but the removal of ammonia was insufficient and fluctuating, making product quality control more difficult. In addition, because ammonia is removed in the freeze drying step under vacuum, the apparatuses in the step are damaged more easily, demanding frequent maintenance and thus, increasing the running cost and making the system less attractive economically. Further, ammonia had a problem in difficulty of product quality control, because the ammonia content of living earthworm varies seasonally and ammonia may cause gastritis when it remains even in a small amount. In the method according to the present invention, most ammonia is removed before freeze drying under vacuum and ammonia remaining in a small amount is also removed completely by freeze drying under vacuum, advantageously giving a uniform-quality product.

Then, the living bodies of the earthworms after practically complete removal of the dirt are washed with purified water and then ground into liquid or paste-like homogenate. The grinding is carried out, for example, in a homogenizer, blender, homomixer, mashing machine, or high-pressure cell mill, normally at a temperature of 1 to 25° C. or, preferably, 2 to 15° C. The homogenate is then placed and dried in a stainless steel tray. Since the enzymes contained in the living body of the earthworm are inactive when the cells are still alive, but react instantaneously with dead cells to generate heat and strong foul odor by putrefaction, for prevention thereof, it is required to use freeze-drying under vacuum process in which the homogenate can be cooled rapidly to a temperature of −18° C. to −35° C. and the enzyme activities are restricted.

For pulverization without deterioration in the pharmacological action inherent to the earthworm, the homogenate should be frozen rapidly, but, on the other hand, freezing in an excessively short period of time or extremely rapid freezing is also unfavorable, because impurities present together with proteins which are principal components of the earthworm paste may form spotty unfrozen regions and may not be separated. For that reason, the freezing is performed favorably at a low temperature of −18° C. to −35° C. over a period of 20 to 240 hours, preferably 50 to 170 hours.

During freeze drying under vacuum, it is important to select a condition allowing favorable removal of water as well as impurities. For that purpose, it is advantageous to perform freeze drying under vacuum by increasing the temperature stepwise in the range of −60° C. to +90° C. under a pressure of 50 Pa or less taking 10 to 60 hours.

For example as described above, the homogenate is frozen at a temperature of −18° C. to −35° C. over a period of 20 to 240 hours and freeze drying under vacuum is performed for 10 to 60 hours by changing a temperature and a pressure stepwise in the range of −60° C. to +90° C. and 4 to 80 Pa, respectively, to obtain a pale yellow dry earthworm powder in the sterile state. The deaeration then is performed by vacuum aspiration.

In the method according to the present invention, it is possible to shorten the freeze-drying period, which traditionally took 100 hours or more, significantly by selecting the drying condition as described above.

The dry earthworm powder thus obtained contains arginine in an amount of 70 to 120 mg, lysine of 110 to 150 mg, histidine of 35 to 60 mg, phenylalanine of 55 to 80 mg, tyrosine of 50 to 75 mg, leucine of 100 to 150 mg, isoleucine of 60 to 90 mg, methionine of 25 to 40 mg, valine of 70 to 105 mg, alanine of 85 to 135 mg, glycine of 75 to 105 mg, proline of 60 to 85 mg, glutamic acid of 210 to 300 mg, serine of 80 to 110 mg, threonine of 75 to 110 mg, aspartic acid of 150 to 220 mg, tryptophan of 15 to 30 mg and cystine of 20 to 35 mg in 100 g of the powder, although the composition may vary slightly according to the kind of the earthworm used and the sampling site and period.

INDUSTRIAL APPLICABILITY

According to the method of the present invention, it is possible to remove the dirt or the excretion of living earthworms by using their natural behavior without any man-made action and also to obtain favorable dry earthworm powder containing no microbe or a foul odor such as of ammonia and containing only a limited amount of arsenic. In addition, the dry earthworm powder obtained by the method according to the present invention contains enzymes at activities of about 1.2 to 1.5 times higher than those of the powder obtained by conventional methods, and shows higher permeability into cells.

Similarly to dry earthworm powders prepared by conventional methods, the dry earthworm powder prepared by the method according to the present invention is useful as a blood pressure-adjusting agent, an anti-hyperlipidemia agent, an anti-diabetes agent, a thrombolytic agent or the like. Active ingredients separated from the dry earthworm powder may be used in applications such as whitener, anti-wrinkling agent, anti-eczema agent, and athlete's foot-treating agent.

Hereinafter, the best modes of carrying out the present invention will be described.

EXAMPLE 1

30 kg of living earthworms of *Lumbricus rubellus* were placed and spread to a thickness of approximately 5 cm in a flat box and exposed to fluorescent lamp irradiation for 24 hours; the living earthworms were covered with a nonwoven fabric, allowing adsorption of the dirt and the excretion accumulated on the skin with the nonwoven fabric, and then washed with water. Subsequently, 250 g of citric acid powder was scattered uniformly thereon, and after 15 seconds, the earthworm mixture was diluted with 30 liter of purified water. The pH immediately after addition of water was 2.25, while the pH at the end of dilution was 2.74.

Then, the earthworms immersed in the diluted citric acid was left still at 20° C. for 60 minutes, when the earthworms, to modify the living environment unpleasant to themselves, excrete the body fluid and the digest in the digestive tracts out of the body as well as ammonia, a cause of foul odor, and arsenic, a compound hazardous to the body.

Conventionally, it was required to immerse earthworms in an aqueous citric acid solution at pH 3 to 6 for at least one hour, resulting in weakening of the earthworms and increase in loss thereof, but brief contact with high-concentration citric acid resulted in almost complete elimination of ammonia without weakening of the earthworms.

The living earthworms were then separated from the dirty aqueous citrate solution, washed with water, and ground into an earthworm paste at 10° C. by using a homogenizer. Then, the earthworm paste was placed in a stainless steel tray, cooled instantaneously to −30° C., and kept at the same temperature, allowing gradual freezing over a period of 50 hours.

The freeze drying under vacuum was performed in such a manner that the earthworm paste thus frozen was kept standing at a temperature of −35° C. under gradually reduced pressure down to 50 Pa taking 3 hours, and the frozen earthworm paste was heated stepwise at a temperature of 20° C. under a pressure of 40 Pa for 12 hours, at a temperature of 40° C. under a pressure of 35 Pa for 25 hours, and finally at a temperature of 80° C. under a pressure of 20 Pa for 5 hours. The processing gave a pale yellow dry earthworm powder having a water content of 8% by mass. The amino acid contents of the dry powder thus obtained are shown in Table 1.

EXAMPLE 2

A pale yellow dry earthworm powder was obtained in a similar manner to Example 1, except that 30 kg of the earthworms of *Lumbricus rubellus* in Example 1 were replaced with 30 kg of those of *Lumbricus terrestris*. The amino acid contents of the dry powders thus obtained are shown in Table 1.

TABLE 1

AMINO ACID CONTENT

| Example | Example 1 | Example 2 (unit: mg/100 g) |
|---|---|---|
| Arginine | 114 | 72.5 |
| Lysine | 148 | 128 |
| Histidine | 55 | 40 |
| Phenylalanine | 77 | 62.5 |
| Tyrosine | 73 | 57 |
| Leucine | 145 | 119.5 |
| Isoleucine | 87 | 74 |
| Methionine | 35 | 33 |
| Valine | 104 | 89 |
| Alanine | 131 | 98 |
| Glycine | 103 | 82.5 |
| Proline | 83 | 65.5 |
| Glutamic acid | 296 | 245.5 |
| Serine | 105 | 87 |
| Threonine | 104 | 81.5 |
| Aspartic acid | 212 | 167 |
| Tryptophan | 28 | 20 |
| Cystine | 32 | 21.5 |

EXAMPLE 3

A dark yellow dry earthworm powder in a composition similar to that of the powder obtained in Example 1 was obtained in a similar manner to Example 1, except that 250 g of citric acid was replaced with 160 g of succinic acid.

REFERENCE EXAMPLE

The dry earthworm powder obtained in Example 1 was processed by the method described in the Example of JP2716472B, to give a purified protease.

To 0.5 μg of the purified protease, added was purified human plasminogen (manufactured by KABIAB, 0.05 CU) for reaction, and the plasmin activity after the reaction was determined. Subsequently, the plasmin hydrolytic activity, as determined from the difference between when the purified protease was added and not added, was 0.145 nmol/minute. The plasmin hydrolytic activity, as determined for comparison similarly by using the purified protease prepared from the dry earthworm powder according to the conventional method described in the patent publication described above, was 0.112 nmol/minute, indicating that the enzyme activity derived from the dry earthworm powder prepared by the method according to the present invention was approximately 1.3 times higher.

What is claimed is:

1. A method of producing a dry earthworm powder comprising:
    standing living earthworms under light for 10 to 50 hours;
    removing the dirt formed on the skin of the earthworms;
    adding an organic acid to the living earthworms;
    diluting the acid rapidly with addition of water to form an aqueous acidic solution;
    performing a pH adjustment on the aqueous acidic solution to a pH in the range of 2 to 5;
    allowing the earthworm mixture to stand for 3 to 180 minutes under said pH;
    washing the earthworms with water;
    grinding the earthworms into a homogenate;
    freezing the homogenate at −18° C. to −35° C.,
    keeping the homogenate for 20 to 240 hours, and
    freeze-drying and degassing the homogenate under a vacuum simultaneously.

2. The method of producing claim 1, wherein the organic acid is selected from the group consisting of acetic acid, malic acid, citric acid, lactic acid, malonic acid, and succinic acid.

* * * * *